(12) United States Patent
Biggs, III et al.

(10) Patent No.: US 9,821,126 B2
(45) Date of Patent: Nov. 21, 2017

(54) FLUID ATOMIZER, NOZZLE ASSEMBLY AND METHODS FOR ASSEMBLING AND UTILIZING THE SAME

(71) Applicant: Neogen Corporation, Lansing, MI (US)

(72) Inventors: James Curtis Biggs, III, Goldsboro, NC (US); Arthur Michael Benton, Jr., Hampstead, NC (US); Paul C. Carney, Oakfield, NY (US)

(73) Assignee: NEOGEN CORPORATION, Lansing, MI (US)

( * ) Notice: Subject to any disclaimer, the term of this patent is extended or adjusted under 35 U.S.C. 154(b) by 584 days.

(21) Appl. No.: 14/186,980

(22) Filed: Feb. 21, 2014

(65) Prior Publication Data

US 2015/0238709 A1 Aug. 27, 2015

(51) Int. Cl.

| A61M 11/06 | (2006.01) |
|---|---|
| A61M 11/00 | (2006.01) |
| A61M 15/08 | (2006.01) |
| B05B 1/34 | (2006.01) |
| B05B 9/01 | (2006.01) |
| B05B 12/00 | (2006.01) |

(Continued)

(52) U.S. Cl.
CPC .......... *A61M 11/006* (2014.02); *A61M 15/08* (2013.01); *B05B 1/34* (2013.01); *B05B 1/3436* (2013.01); *B05B 9/01* (2013.01); *B05B 12/002* (2013.01); *B05B 15/02* (2013.01); *A61M 2207/10* (2013.01); *B05B 9/0894* (2013.01); *Y10T 29/49433* (2015.01)

(58) Field of Classification Search
CPC ....... B05B 1/3442; B05B 1/3431; B05B 1/14; B05B 1/34; A61M 11/006; A61M 15/08

USPC ............................................................ 239/1
See application file for complete search history.

(56) References Cited

U.S. PATENT DOCUMENTS

| 745,178 A | 11/1903 | Gordejeff |
| 995,981 A | 6/1911 | Mills |

(Continued)

FOREIGN PATENT DOCUMENTS

| DE | 1143457 B | 2/1963 |
| FR | 2197659 A1 | 3/1974 |

(Continued)

OTHER PUBLICATIONS

MAI Nasal Sprayer 4" Product No. 02-48-0005.

(Continued)

*Primary Examiner* — Chee-Chong Lee
(74) *Attorney, Agent, or Firm* — Honigman Miller Schwartz and Cohn LLP; Douglas H. Siegel; Jonathan P. O'Brien

(57) ABSTRACT

A method of assembling a nozzle assembly is disclosed. The method includes: providing a nozzle member having a central passage defined by at least an inner side surface and an inner distal surface; inserting a fluid atomizer into the central passage of the nozzle member; and, with a distal surface of the fluid atomizer arranged adjacent the inner distal surface of the nozzle member, flexing legs of the fluid atomizer in a radially-outward direction for engaging each leg of the legs with the inner side surface of the nozzle member. A fluid atomizer is also disclosed. A nozzle assembly is also disclosed. A method of utilizing a nozzle assembly is also disclosed.

29 Claims, 14 Drawing Sheets

(51) Int. Cl.
*B05B 15/02* (2006.01)
*B05B 9/08* (2006.01)

(56) References Cited

U.S. PATENT DOCUMENTS

| | | | |
|---|---|---|---|
| 1,837,339 A | 12/1931 | Schlick | |
| 1,902,225 A | 3/1933 | Forney | |
| 1,940,171 A | 12/1933 | Huss | |
| 2,044,696 A | 6/1936 | Huss | |
| 2,071,920 A | 2/1937 | Czarnecki | |
| 2,107,601 A | 2/1938 | Davis | |
| 2,126,440 A | 8/1938 | Apthorp | |
| 2,307,206 A | 1/1943 | Fischer | |
| 2,562,731 A | 7/1951 | Murphy | |
| 2,823,854 A | 4/1953 | Walther | |
| 2,643,915 A | 6/1953 | Pieroni | |
| 2,823,954 A | 2/1958 | Olson | |
| 2,948,478 A | 8/1960 | Walsh | |
| 3,054,563 A | 9/1962 | Steinen | |
| 3,672,578 A | 6/1972 | Wayne | |
| 3,684,194 A | 8/1972 | Wayne | |
| 3,793,690 A | 2/1974 | Wayne | |
| 3,897,006 A * | 7/1975 | Tada | B05B 11/3074 222/321.8 |
| 3,973,700 A * | 8/1976 | Schmidt | B05B 11/303 222/153.13 |
| 3,995,774 A * | 12/1976 | Cooprider | B05B 11/303 222/207 |
| 4,168,788 A * | 9/1979 | Quinn | B05B 11/0018 222/383.1 |
| 4,199,083 A * | 4/1980 | LoMaglio | B05B 11/303 222/207 |
| 4,260,110 A | 4/1981 | Werding | |
| 4,360,156 A | 11/1982 | Soth et al. | |
| 4,613,079 A | 9/1986 | Mains | |
| 4,624,413 A | 11/1986 | Corsette | |
| 4,736,893 A | 4/1988 | Norskov | |
| 5,143,293 A | 9/1992 | Pairis | |
| 5,303,867 A * | 4/1994 | Peterson | B05B 1/3436 222/207 |
| 5,667,017 A * | 9/1997 | Hoffmann | A62C 37/08 169/37 |
| 5,927,611 A | 7/1999 | Palestrant | |
| 6,000,636 A | 12/1999 | Huang | |
| 6,666,386 B1 | 12/2003 | Huang | |
| 6,863,230 B2 | 3/2005 | Palestrant | |
| 6,953,161 B2 | 10/2005 | Laursen et al. | |
| 2004/0031485 A1* | 2/2004 | Rustad | A61M 11/00 128/200.18 |

FOREIGN PATENT DOCUMENTS

| | | |
|---|---|---|
| GB | 320567 A | 10/1929 |
| WO | 9500252 A1 | 1/1995 |
| WO | WO-0054887 A1 | 9/2000 |

OTHER PUBLICATIONS

LMA/MAD Nasal Intranasal Mucosal Atomization Device, Catalog # MAD300B, Lot: 130725.
International Search Report and Written Opinion for PCT/US2015/016337 dated May 11, 2015.

* cited by examiner

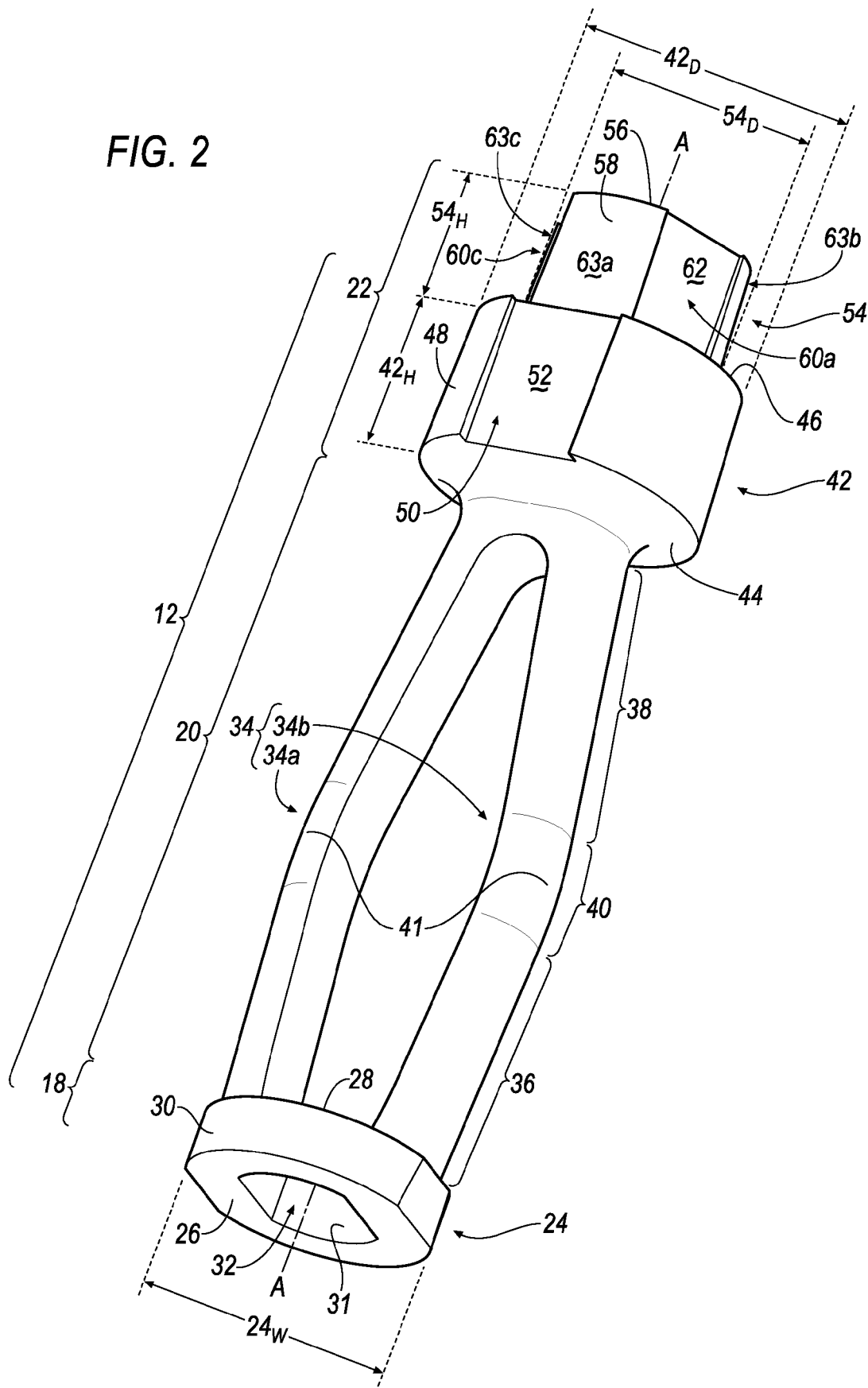

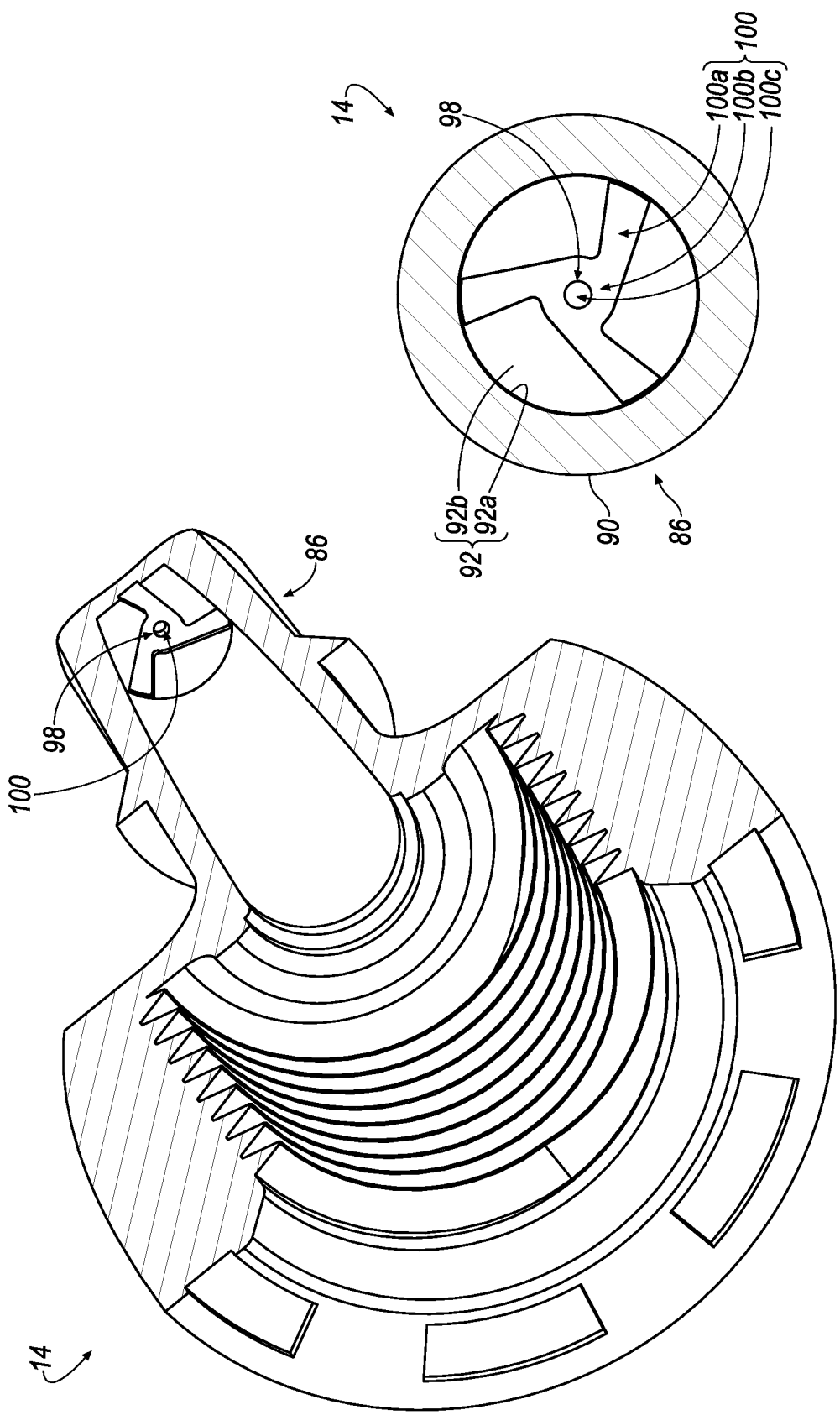

FLUID ATOMIZER, NOZZLE ASSEMBLY AND METHODS FOR ASSEMBLING AND UTILIZING THE SAME

TECHNICAL FIELD

This disclosure relates to a fluid atomizer, nozzle assembly and methods for assembling and utilizing the same.

BACKGROUND

Structures for delivering a fluid are known in the art. Improvements to structures for delivering a fluid are continuously being sought in order to advance the arts.

SUMMARY

One aspect of the disclosure provides a method of assembling a nozzle assembly. The method may include the steps of: providing a nozzle member having a central passage defined by at least an inner side surface and an inner distal surface; inserting a fluid atomizer into the central passage of the nozzle member; and with a distal surface of the fluid atomizer arranged adjacent the inner distal surface of the nozzle member, flexing legs of the fluid atomizer in a radially-outward direction for engaging each leg of the legs with the inner side surface of the nozzle member.

Implementations of the disclosure may include the flexing step being conducted in response to applying an axial force to a proximal surface of the fluid atomizer.

Additionally, the applying step may be conducted in response to inserting a distal portion of a spray gun into the central passage of the nozzle member.

In some examples, the method may include the steps of: providing a conical cap member including an axial passage; and inserting a distal stem portion of the nozzle member through the axial passage of the conical cap member for connecting the conical cap member to the distal stem portion of the nozzle member. One or more radially outwardly projecting barbs may extend from an outer side surface of the distal stem portion of the nozzle member.

In some implementations, the inserting step results in radially engaging and securing the conical cap member for securing the conical cap member to the nozzle member.

In other implementations, the legs of the fluid atomizer may include a pair of opposing legs.

In some instances, engaging each leg of the legs with the inner side surface of the nozzle member results in spatially-fixing the fluid atomizer within the central passage of the nozzle member.

Another aspect of the disclosure provides a fluid atomizer. The fluid atomizer may include a proximal portion having a body, an intermediate portion and a distal portion. The intermediate portion may include legs connected to the body of the proximal portion. The distal portion may include a shoulder portion connected to the legs of the intermediate portion. The intermediate portion may be between the proximal portion and the distal portion. The distal portion may further include a head portion adjacent to the shoulder portion.

Implementations of the disclosure may include the proximal portion being integrally-formed with the intermediate portion. The intermediate portion may be integrally-formed with the distal portion.

Additionally, the body may include: a proximal surface, a distal surface, an outer side surface and an inner side surface. The inner side surface defines a passage that extends through the body from the proximal surface to the distal surface.

In some examples, each leg of the legs may include: a proximal portion, a distal portion and an intermediate knee portion between the proximal portion and the distal portion. The proximal portion of each leg of the legs may be integral with and extends away from the distal surface of the body.

In some implementations, as each of the proximal portion and the distal portion of each leg of the legs extend axially away from the proximal portion and the distal portion, each of the proximal portion and the distal portion of each leg of the legs extend with a radially outward component such that the intermediate knee portion of each leg defines a peak of each leg that may be arranged at a position that may be radially beyond a width defined by the side surface of the body.

In other implementations, the distal portion of each leg of the legs may be integral with and extend away from a proximal surface of the shoulder portion of the distal portion.

In some instances, the shoulder portion may further include a distal surface and a side surface between the proximal surface of the shoulder portion and the distal surface of the shoulder portion.

Implementations of the disclosure may include the side surface of the shoulder portion forming a radially inwardly projecting recess that extends along an entire height of the shoulder portion.

Additionally, the head portion may axially extend from and may be integral with distal surface of the shoulder portion. The head portion may include a distal surface and a side surface between the distal surface of the head portion and the distal surface of the shoulder portion.

In some examples, the side surface of the head portion may be interrupted by a plurality of radially inwardly projecting recesses and a plurality of arcuate surfaces. Each arcuate surface of the plurality of arcuate surfaces may be arranged between radially inwardly projecting recesses of the plurality of radially inwardly projecting recesses.

In some implementations, one of the arcuate surfaces of the plurality of arcuate surfaces of the head portion may be aligned with the radially inwardly projecting recess of the shoulder portion.

In other implementations, the body of the proximal portion may be a substantially circular body.

In some instances, the legs of the intermediate portion may include a pair of opposing legs.

In still yet another aspect of the disclosure provides a nozzle assembly including a nozzle member and a fluid atomizer. The nozzle member may include a proximal base portion and a distal stem portion. The proximal base portion may include an inner side surface that defines a passage that extends axially through the proximal base portion. The distal stem portion may include an inner side surface that defines a passage that extends through the distal stem portion. The fluid atomizer may include a proximal portion, an intermediate portion and a distal portion. The proximal portion may include a body. The intermediate portion may include legs connected to the body of the proximal portion. The distal portion may include a shoulder portion connected to the legs of the intermediate portion. The intermediate portion may be between the proximal portion and the distal portion. The distal portion may further include a head portion adjacent to the shoulder portion. The fluid atomizer may be configured to connect to the nozzle member when the fluid atomizer is arranged within the passage that extends through the distal stem portion of the nozzle member.

Implementations of the disclosure may include a conical cap member including an axial passage configured to accept insertion of the distal stem portion of the nozzle member therethrough.

Additionally, the conical cap member may be formed from a soft, resilient material.

In some examples, one or more radially outwardly projecting barbs may extend from an outer side surface of the distal stem portion of the nozzle member to radially engage the conical cap member to the nozzle member.

In some implementations, the body of the proximal portion may include a substantially circular body.

In other implementations, the legs of the intermediate portion may include a pair of opposing legs.

In yet another aspect of the disclosure provides a method of utilizing a nozzle assembly includes the steps of: providing a nozzle member having a central passage defined by at least an inner side surface and an inner distal surface; assembling the nozzle assembly by inserting a fluid atomizer into the central passage of the nozzle member; inserting a distal portion of a spray gun into the central passage of the nozzle member for: firstly urging a distal surface of the fluid atomizer adjacent the inner distal surface of the nozzle member then secondly flexing legs of the fluid atomizer in a radially-outward direction in response to an application of an axial force to a proximal surface of the fluid atomizer for radially engaging the legs with the inner side surface of the nozzle member; actuating the spray gun for causing a fluid to travel from the spray gun through the central passage of the nozzle member; atomizing the fluid as the fluid travels through the central passage of the nozzle member; and permitting the fluid to travel beyond the fluid atomizer and out of the nozzle member in an atomized spray pattern.

Additionally, prior to the actuating step, the method includes arranging the nozzle assembly within a nasal passage of animalia. The fluid may be a drug, medicine or vaccination that may be delivered into the nasal passage of the animalia in the atomized spray pattern.

In some examples, the spray pattern may include fluid droplets. The fluid droplets may be defined by: a D10 particle size distribution value, a D50 particle size distribution value and a D90 particle size distribution value. The D10 particle size distribution value is greater than approximately 15 um (microns). The D50 particle size distribution value ranges between approximately 50-65 um (microns). The D90 particle size distribution value is less than approximately 200 um (microns).

In some implementations, the D10 particle size distribution value ranges between approximately 15-25 um, and, the D50 particle size distribution value ranges between approximately 50-60 um, and, the D90 particle size distribution value ranges between approximately 180-200 um (microns).

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2 is a perspective view of an atomizer of the nozzle assembly of FIGS. 1A-1B.

FIG. 6 is a perspective, cross-sectional view of the nozzle member of FIG. 5.

FIG. 7 is a cross-sectional view of the nozzle member according to line 7-7 of FIG. 4.

FIG. 8B' is an enlarged view of FIG. 8B according to line 8B'.

FIG. 8C' is an enlarged view of FIG. 8C according to line 8C'.

FIG. 8D' is an enlarged view of FIG. 8D according to line 8D'.

Like reference symbols in the various drawings indicate like elements.

DETAILED DESCRIPTION

Figure 1A:
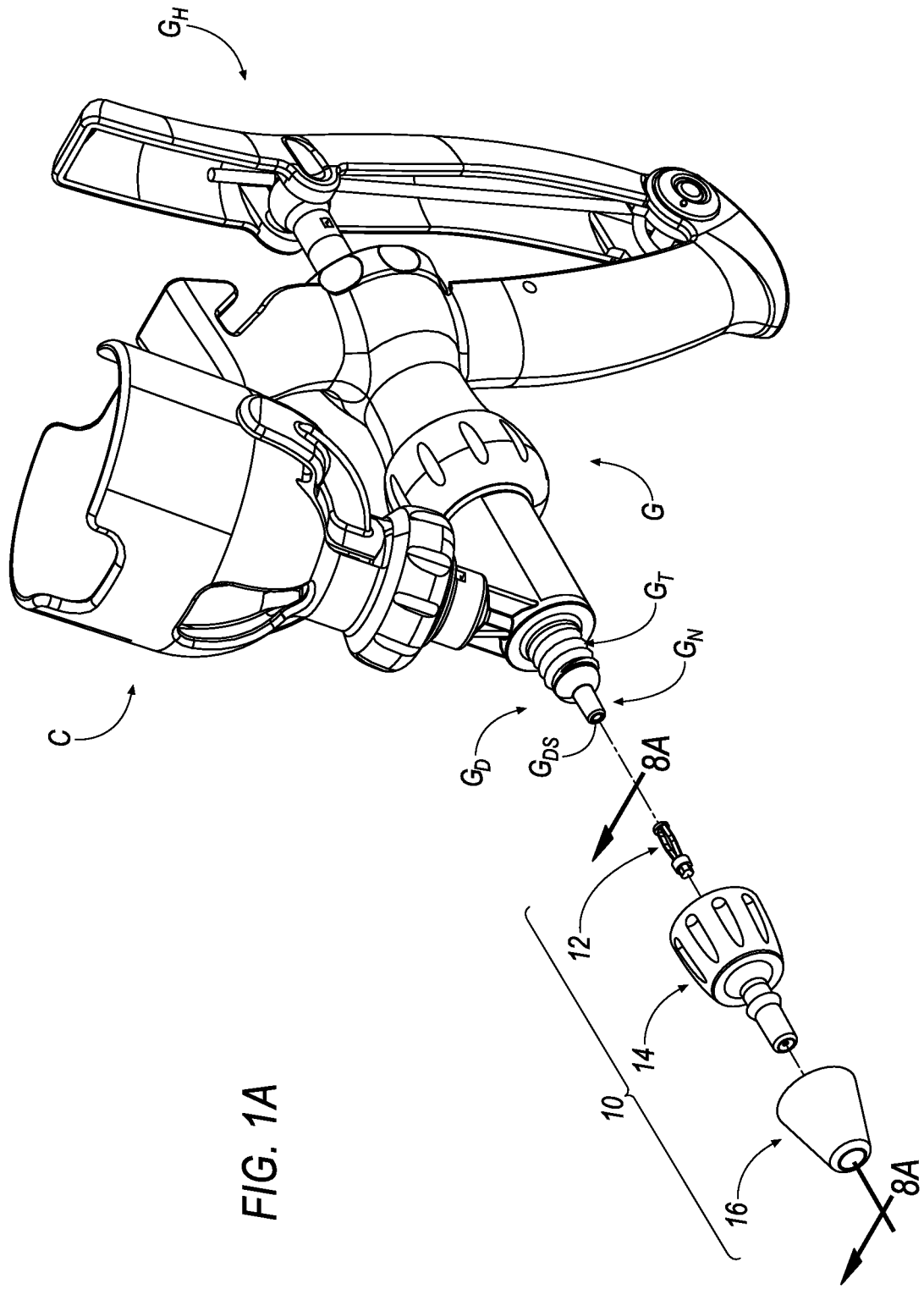
FIG. 1A is an exploded perspective view of an exemplary nozzle assembly and spray gun.
Figure 1B:
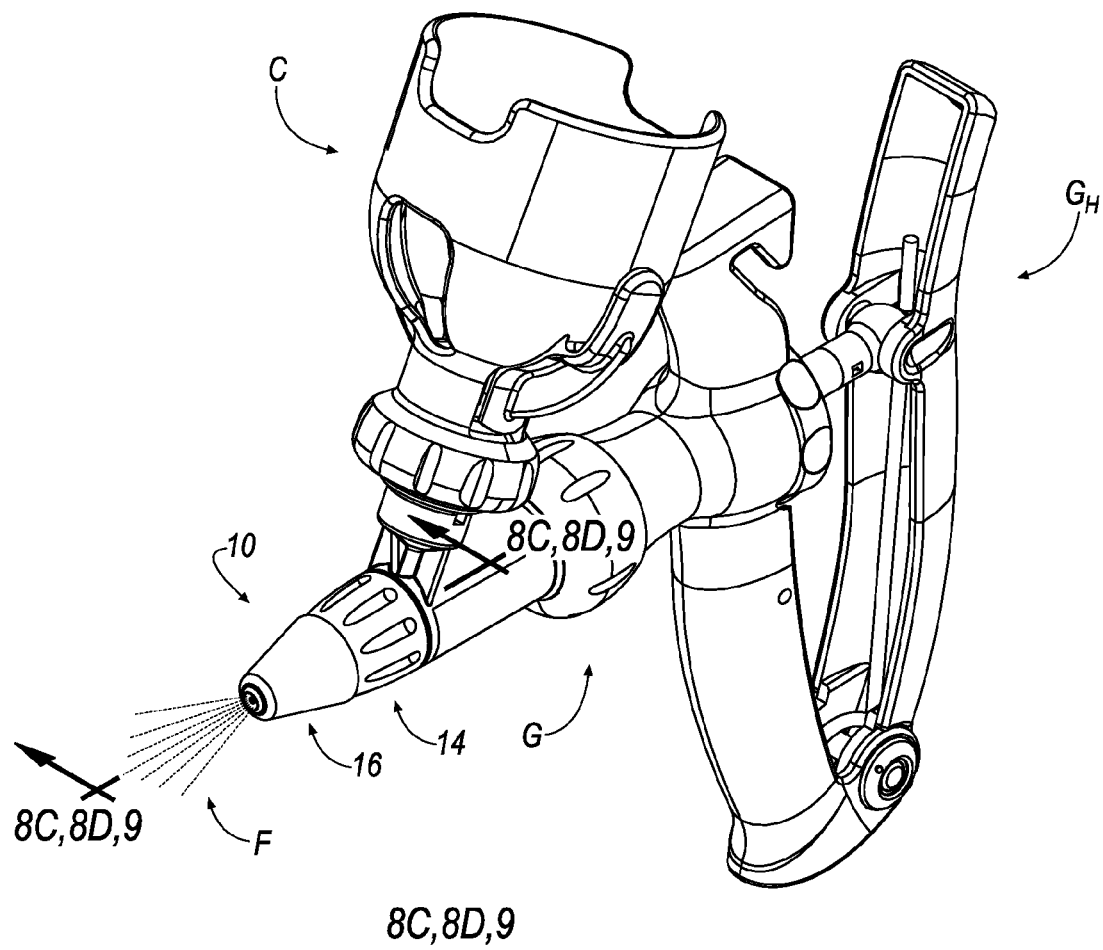
FIG. 1B is an assembled perspective view of the nozzle assembly that is attached to the spray gun of FIG. 1A.

Referring to FIGS. 1A-1B, a nozzle assembly 10 may be removably-connected to a spray gun, G. As will be described in the following disclosure at FIGS. 8C-8D, the nozzle assembly 10 may be removably-connected to the spray gun, G.

As seen in FIG. 1A, in some implementations, the nozzle assembly 10 includes a first portion 12, a second portion 14 and a third portion 16. In some examples, the first portion 12 is a fluid atomizer. In some examples, the second portion 14 is a nozzle member that receivably-contains the fluid atomizer 12 (as seen in, e.g., FIGS. 8B-8D). In some examples, the third portion 16 is a conical cap member that is connected to and disposed about an outer surface portion of a distal end of the nozzle member 14 (as seen in, e.g., FIGS. 1B and 8B-8D). The conical cap member 16 may be made of a soft, resilient material (e.g., foam, rubber or the like).

Referring to FIG. 1B, upon actuating the spray gun, G (by, e.g., pressing a handle member, $G_H$, of the spray gun, G), fluid, F, may be guided from a fluid container, C (that is attached to the spray gun, G), through the spray gun, G, and out of the nozzle assembly 10 such that the fluid, F, may be sprayed in a pattern. The spray pattern is determined, at least in part, by an outer surface profile of the fluid atomizer 12 and an inner surface fluid conduit profile of the nozzle member 14. Although the container, C, is shown mounted to a top portion of the spray gun, G, the mounting location of the container, C, is not limited to what is shown in the Figures; for example in some instances, the container, C, may be a tube-shaped structure (not shown) that is mounted to a rear portion of the spray gun, G.

In some instances, the spray pattern may be defined by fluid droplets. The fluid droplets may be described in terms of particle size distributions (i.e., 'D values'). 'D values' of D10, D50 and D90 may be used to represent the midpoint and range of particle sizes of a given sample. The D10 particle size is the diameter at which 10% of a sample's mass is comprised of smaller particles. The D50 may be known as the 'mass median diameter' as it divides the sample equally by mass. The D90 particle size is the diameter at which 90% of a sample's mass is comprised of smaller particles. In some examples, the D10 particle size may be greater than approximately 15 um (microns) in order to minimize tracheobronchial and deep lung deposition while maintaining a high nasal fraction; and in some examples, the D10 particle size may range between approximately 15-25 um. In some instances, the D50 particle size may range between approximately 50-65 um (microns) in order to maximize nasal deposition; and in some instances the D50 particle size may range between approximately 50-60 um. In some implementations, the D90 particle size may be less than approximately 200 um (microns) in order to minimize gastrointestinal dosage; and in some implementations the D90 particle size may range between approximately 180-200 um.

In some instances, prior to actuating the spray gun, G, a distal portion of the nozzle assembly (e.g., including conical cap member 16 attached to the nozzle member 14) may be arranged within nasal passage (not shown) of animalia. Animalia may include any animal species including, but not limited to: humans, swine, cows, horses or the like. The fluid, F, that is dispensed from the nozzle assembly 10 in a spray pattern may be directed into the nasal passage for administering a drug, medicine, vaccination or the like to the animalia.

After one or more uses of the spray gun, G, as described above, a user may disconnect the nozzle assembly 10 from the spray gun, G, in order to unclog or clean the nozzle assembly 10 of obstructions and contaminates, such as, for example, mucus. As will be described in the following disclosure, upon disconnecting the nozzle assembly 10 from the spray gun, G, the components 12, 14, 16 of nozzle assembly 10 may easily separate in order to access and clean each component 12, 14, 16 of nozzle assembly 10.

Referring to FIGS. 2 and 3A-3C, an exemplary fluid atomizer 12 is shown according to an embodiment. As seen in FIG. 2, the fluid atomizer 12 generally includes one-piece integral body having a proximal portion 18, an intermediate portion 20 and a distal portion 22. A central axis, A-A, is shown extending through an axial center of the fluid atomizer 12.

The proximal portion 18 includes a substantially circular body 24 having a proximal surface 26 and a distal surface 28. The substantially circular body 24 also includes an outer side surface 30 and an inner side surface 31 that both connect the proximal surface 26 to the distal surface 28. The outer side surface 30 may define the substantially circular body 24 to include a width $\mathbf{24}_W$. The inner side surface 31 defines a passage 32 that extends through the substantially circular body 24 from the proximal surface 26 to the distal surface 28.

The intermediate portion 20 includes a pair of opposing legs 34. Each leg 34*a*, 34*b* includes a proximal portion 36, a distal portion 38 and an intermediate knee portion 40 that joins the proximal portion 36 to the distal portion 38. The proximal portion 36 of each leg 34*a*, 34*b* is integral with and extends away from the distal surface 28 of the substantially circular body 24. The distal portion 38 of each leg 34*a*, 34*b* is integral with and extends away from a proximal surface 44 of a shoulder portion 42 of the distal portion 22. As each of the proximal portion 36 and the distal portion 38 of each leg 34*a*, 34*b* extends axially away from the proximal portion 18 and the distal portion 22 as described above, each of the proximal portion 36 and the distal portion 38 of each leg 34*a*, 34*b* extends with a radially outward component such that the intermediate knee portion 40 of each leg 34*a*, 34*b* defines a peak 41 of each leg 34*a*, 34*b* that is arranged at a position that may be radially beyond the width $\mathbf{24}_W$ defined by the side surface 30 of the substantially circular body 24.

The distal portion 22 includes a shoulder portion 42. The shoulder portion 42 includes a proximal surface 44, a distal surface 46 and a side surface 48 connecting the proximal surface 44 to the distal surface 46. The side surface 48 may define the shoulder portion 42 to include a diameter $\mathbf{42}_D$. In some instances, the diameter $\mathbf{42}_D$ may subtly narrow along a height $\mathbf{42}_H$ of the shoulder portion 42 as the shoulder portion 42 axially extends from the proximal surface 44 toward the distal surface 46. The diameter $\mathbf{42}_D$ defined by the side surface 48 is interrupted by a radially inwardly projecting recess 50 formed in the side surface 48. The radially inwardly projecting recess 50 may be defined by a flat surface 52 that extends along the entire height $\mathbf{42}_H$ of the shoulder portion 42.

The distal portion 22 also includes a head portion 54 that axially extends from and is integral with distal surface 46 of the shoulder portion 42. The head portion 54 includes a distal surface 56 and a side surface 58 connecting the distal surface 56 of the head portion 54 to the distal surface 46 of the shoulder portion 42. The side surface 58 may define the head portion 54 to include a diameter $\mathbf{54}_D$. In some instances, the diameter $\mathbf{54}_D$ may subtly narrow along a height $\mathbf{54}_H$ of the head portion 54 as the head portion 54 axially extends from the distal surface 46 of the shoulder portion 42 toward the distal surface 56 of the head portion 54.

Referring to FIG. 3C, the side surface 58 is interrupted by a plurality of radially inwardly projecting recesses 60 formed in the side surface 58. Each radially inwardly projecting recess 60*a*, 60*b*, 60*c* of the plurality of radially inwardly projecting recesses 60 may be defined by a flat surface 62 that extends along the entire height $\mathbf{54}_H$ of the head portion 54. As a result of the formation of the plurality of radially inwardly projecting recesses 60, the side surface 58 of the head portion 54 includes a plurality of arcuate surfaces 63 that generally define the diameter $\mathbf{54}_D$ defined by the side surface 58.

In some implementations, the plurality of radially inwardly projecting recesses 60 are defined by three radially inwardly projecting recesses 60*a*-60*c* including a first radially inwardly projecting recess 60*a*, a second radially inwardly projecting recess 60*b* and a third radially inwardly projecting recess 60*c*. In some implementations the plurality of actuate surfaces 63 are defined by three arcuate surfaces 63*a*-63*c* including a first arcuate surface 63*a*, a second arcuate surface 63*b* and a third arcuate surface 63*c*. As seen in FIGS. 2 and 3C, in some examples, one of the arcuate surfaces 63*a*-63*c* (e.g., the first arcuate surface 63*a*) of the plurality of arcuate surfaces 63 of the head portion 54 is aligned with the radially inwardly projecting recess 50 of the shoulder portion 42.

Referring to FIGS. 4-7, an exemplary nozzle member 14 is shown according to an embodiment. The nozzle member 14 generally includes one-piece integral body having a proximal base portion 64 and a distal stem portion 66. A central axis, A-A, is shown at FIGS. 4-6 extending through an axial center of the nozzle member 14.

Figure 4:
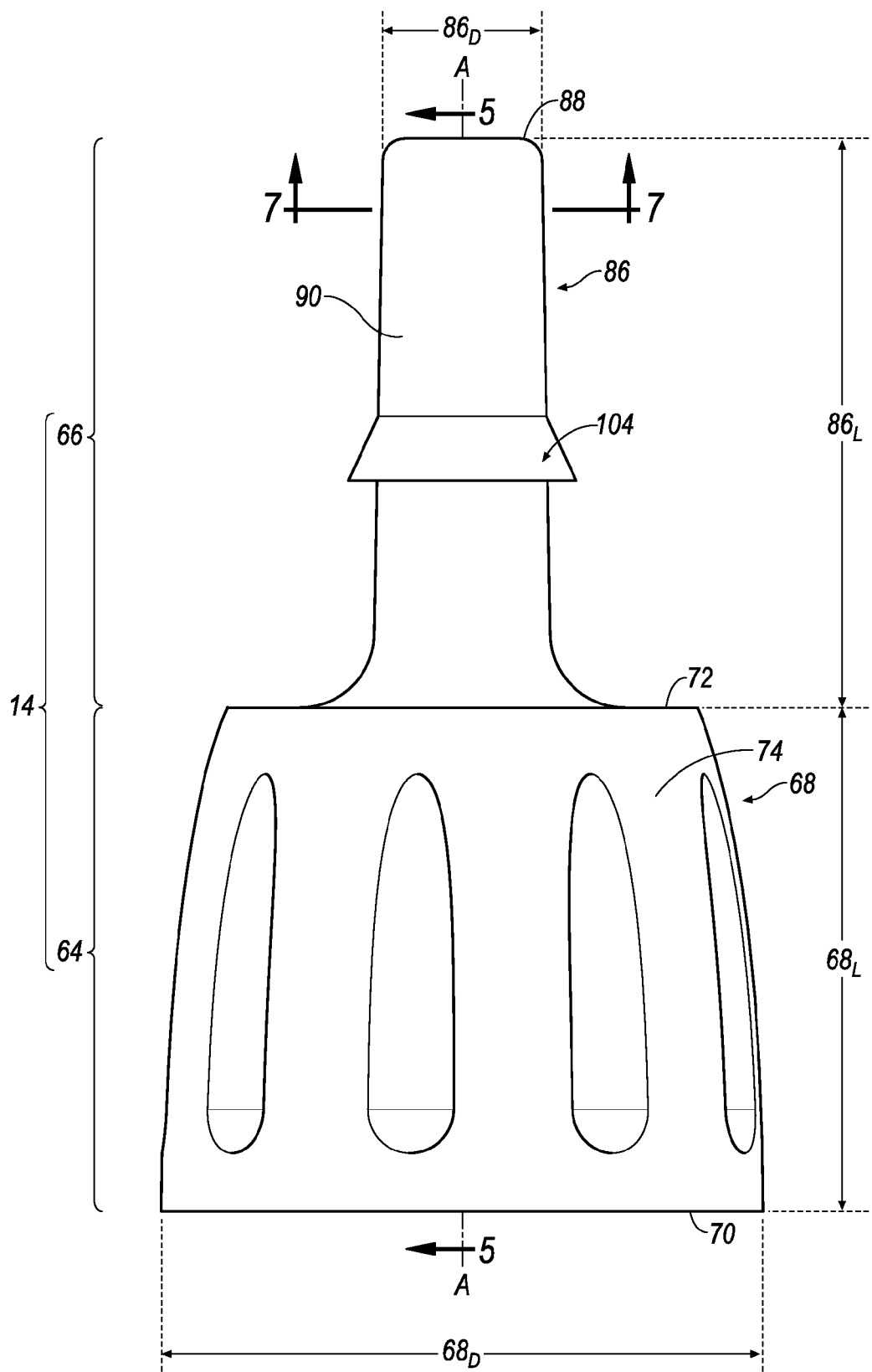
FIG. 4 is a side view of a nozzle member of the nozzle assembly of FIGS. 1A-1B.
Figure 5:
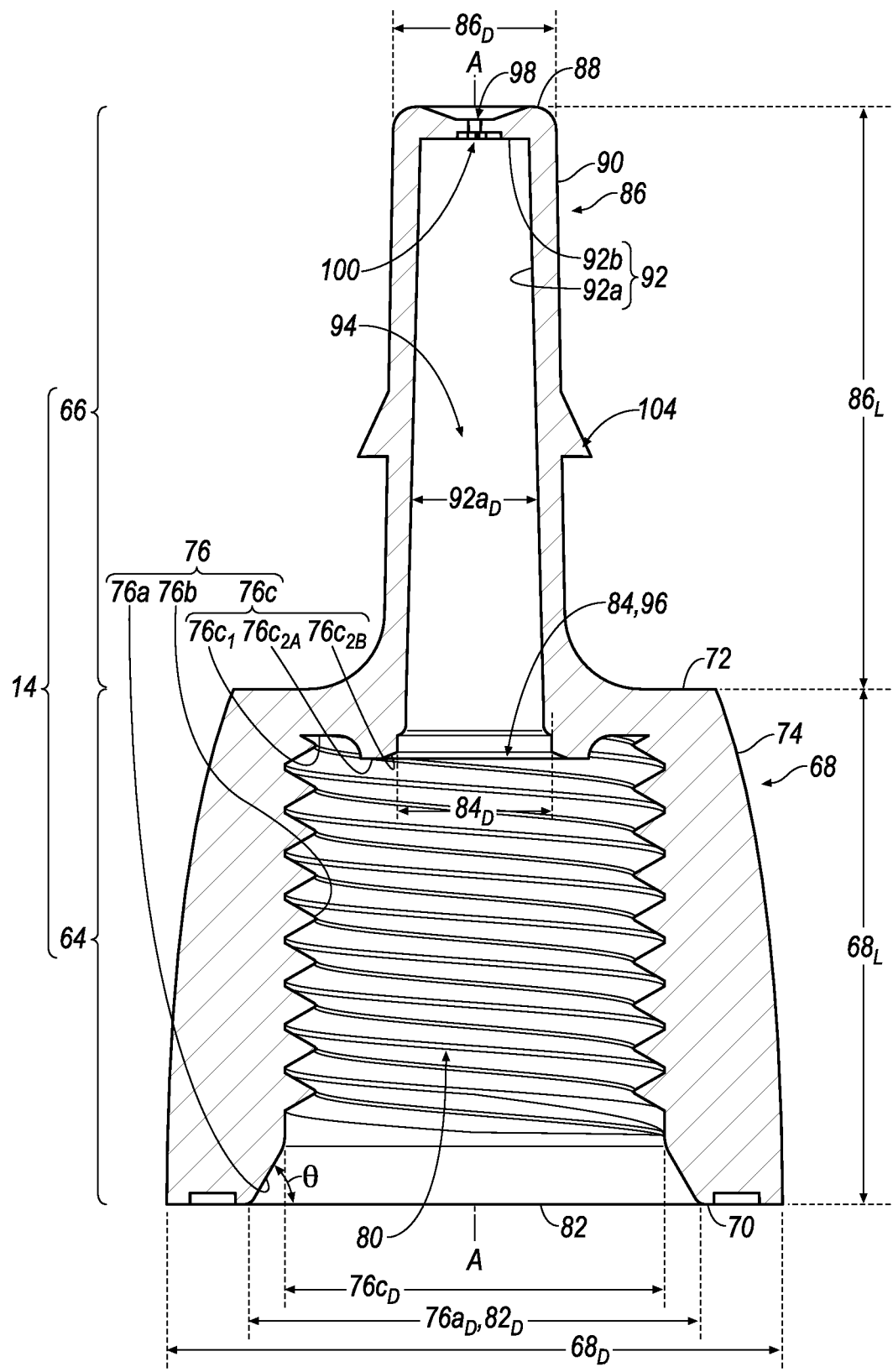
FIG. 5 is a cross-sectional view of the nozzle member according to line 5-5 of FIG. 4.

Referring to FIGS. 4-5, the proximal base portion 64 includes a substantially tube-shaped body 68 having a proximal outer surface 70 and a distal outer surface 72. The substantially tube-shaped body 68 also includes an outer side surface 74. The outer side surface 74 may define the substantially tube-shaped body 68 to include a diameter $68_D$. The outer side surface 74 connects the proximal outer surface 70 to the distal outer surface 72.

Referring to FIG. 5, the substantially tube-shaped body 68 further includes an inner surface 76. The inner surface 76 is defined by an inner chamfered side surface 76a, an inner side surface 76b and an inner distal surface 76c. The inner chamfered side surface 76a includes a substantially conical surface portion connecting the proximal outer surface 70 to the inner side surface 76b; the inner chamfered side surface 76a extends away from the proximal outer surface 70 at an angle, θ, which may range between approximately an angle greater than 0° and an angle less than 90°. The inner side surface 76b includes a threaded surface. The inner distal surface 76c includes a substantially flat surface portion $76c_1$ extending radially inwardly from the inner side surface 76b toward the central axis, A-A. The inner distal surface 76c also includes a substantially circumferential rib portion (see, e.g., reference numerals $76c_{2A}$, $76c_{2B}$) that circumscribes the central axis, A-A, and projects axially away from the substantially flat surface portion $76c_1$ of the inner distal surface 76b. The circumferential rib portion includes a substantially flat surface portion $76c_{2A}$ connected to the substantially flat surface portion $76c_1$. The circumferential rib portion also includes a chamfered surface portion $76c_{2B}$ that extends radially inwardly from the substantially flat surface portion $76c_{2A}$.

The inner side surface 76 defines a passage 80 that extends through the substantially tube-shaped body 68. In some instances, the passage 80 may extend between the proximal outer surface 70 and the inner distal surface 76c such that the passage 80 extends through approximately about 90% of a length $68_L$ of the substantially tube-shaped body 68. In some instances, the passage 80 includes a substantially constant diameter $76c_D$ defined by threaded inner side surface 76b and a non-constant diameter $76a_D$ defined by the inner chamfered side surface 76a.

Access to the passage 80 is permitted by a proximal passage opening 82 and a distal passage opening 84. The proximal passage opening 82 may be defined by a diameter $82_D$ defined by the connection of the proximal outer surface 70 to the inner chamfered side surface 76a. The distal passage opening 84 may be defined by a diameter $84_D$. In some instances the distal passage opening 84 may be defined by the chamfered surface portion $76c_{2B}$ of the substantially circumferential rib portion of the inner distal surface 76c.

The diameter $82_D$ of the proximal passage opening 82 may be approximately equal to the largest diameter of the non-constant diameter $76a_D$ defined by the inner chamfered side surface 76a. The smallest diameter of the non-constant diameter $76a_D$ defined by the inner chamfered side surface 76a may be approximately equal to the substantially constant diameter $76c_D$ defined by threaded inner side surface 76b. The diameter $84_D$ defined by the distal passage opening 84 is less than the substantially constant diameter $76c_D$ defined by threaded inner side surface 76b.

With reference to FIGS. 4-5, the distal stem portion 66 includes a substantially tube-shaped body 86 having a distal outer surface 88 and an outer side surface 90. The outer side surface 90 may define the substantially tube-shaped body 86 to include a diameter $86_D$. The outer side surface 90 connects the distal outer surface 72 of the tube-shaped body 68 of the proximal base portion 64 to the distal outer surface 88 of the substantially tube-shaped body 86 of the distal stem portion 66.

Referring to FIG. 5, the substantially tube-shaped body 86 further includes an inner surface 92. The inner surface 92 is defined by an inner side surface 92a and an inner distal surface 92b. The inner side surface 92a includes a substantially circular surface portion that is connected to and extends axially away from the chamfered surface portion $76c_{2B}$ of the substantially circumferential rib portion of the inner distal surface 76c of the substantially tube-shaped body 68 of the proximal base portion 64. The inner distal surface 92b includes a substantially flat surface portion extending perpendicularly from the inner side surface 92a.

The inner side surface 92 defines a passage 94 that extends through the substantially tube-shaped body 86. In some instances, the passage 94 may extend between the chamfered surface portion $76c_{2B}$ of the substantially circumferential rib portion of the inner distal surface 76c of the substantially tube-shaped body 68 of the proximal base portion 64 and the inner distal surface 92b such that the passage 94 extends through approximately about 90% of a length $86_L$ of the substantially tube-shaped body 86. In some instances, passage 94 includes a substantially constant diameter $92a_D$ defined by substantially circular surface portion 92a.

Access to the passage 94 is permitted by a proximal passage opening 96 and a distal passage opening 98. The proximal passage opening 96 is substantially equal to and may be defined by the diameter $84_D$ formed by the chamfered surface portion $76c_{2B}$ of the substantially circumferential rib portion of the inner distal surface 76c as described above. The proximal passage opening 96 may be slightly greater than the substantially constant diameter $92a_D$ defined by the substantially flat surface portion 92a of the inner side surface 92 of the substantially tube-shaped body 86 of the distal stem portion 66.

Referring to FIGS. 6-7, the distal passage opening 98 is defined by a recess 100 formed in the inner distal surface 92b of the inner side surface 92 of the substantially tube-shaped body 86 of the distal stem portion 66. Referring to FIG. 7, the recess 100 is defined by a plurality of radial recess portions 100a, a central recess portion 100b and an axial recess passage portion 100c. The plurality of radial recess portions 100a radially converge upon and are fluidly connected to the central recess portion 100b, and, the axial recess passage portion 100c is fluidly connected to the central recess portion 100b. In some examples, the plurality of radial recess portions 100a may include three radial recess portions that are angularly spaced apart by approximately 120°.

With reference to FIG. 5, the passages 80, 94 and openings 82, 84, 96, 98 described above permit the nozzle member 14 to guide movement of the fluid, F, through the nozzle assembly 10. For example, the proximal passage opening 82 of the passage 80 formed by the proximal base portion 64 permits fluid to enter the nozzle member 14. Once the fluid has entered the nozzle member 14, the passage 80 formed by the proximal base portion 64 is in fluid communication with the passage 94 formed by the distal stem portion 66, and, therefore, the passages 80, 94 cooperate by guiding the fluid, F, as the fluid, F, travels through the nozzle member 14 after entering the proximal passage opening 82 of the passage 80. Thereafter, the distal passage opening 98 of the passage 94 formed by the distal stem portion 66 permits fluid to exit the nozzle member 14.

Figure 3A:
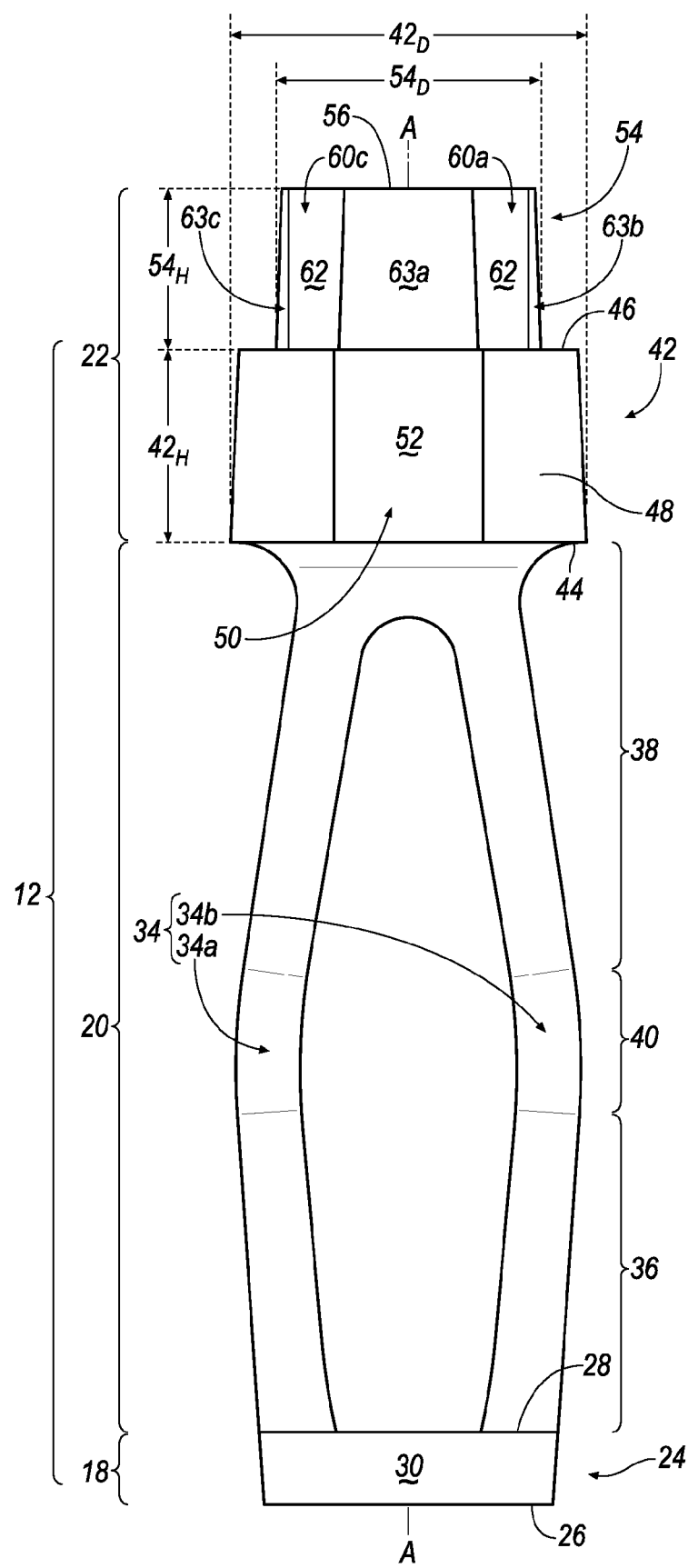
FIG. 3A is a side view of the atomizer of FIG. 2.
Figure 3B:
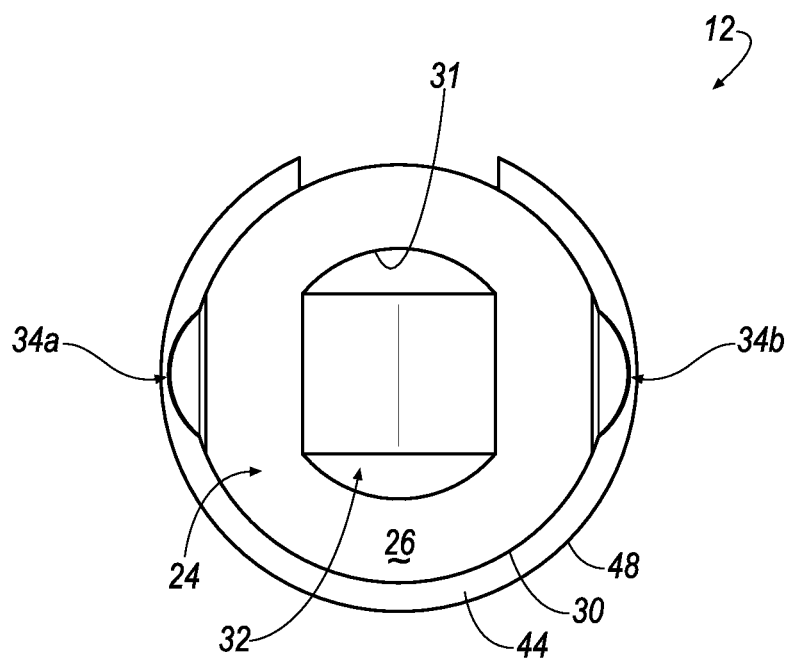
FIG. 3B is a bottom end view of the atomizer of FIG. 2
Figure 3C:
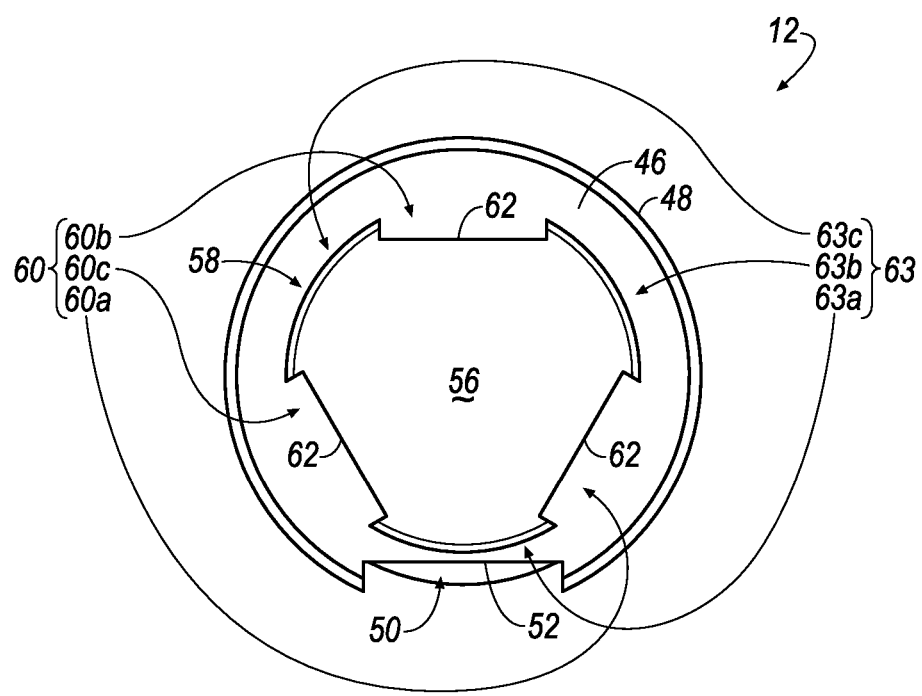
FIG. 3C is a top end view of the atomizer of FIG. 2.
Figure 8A:
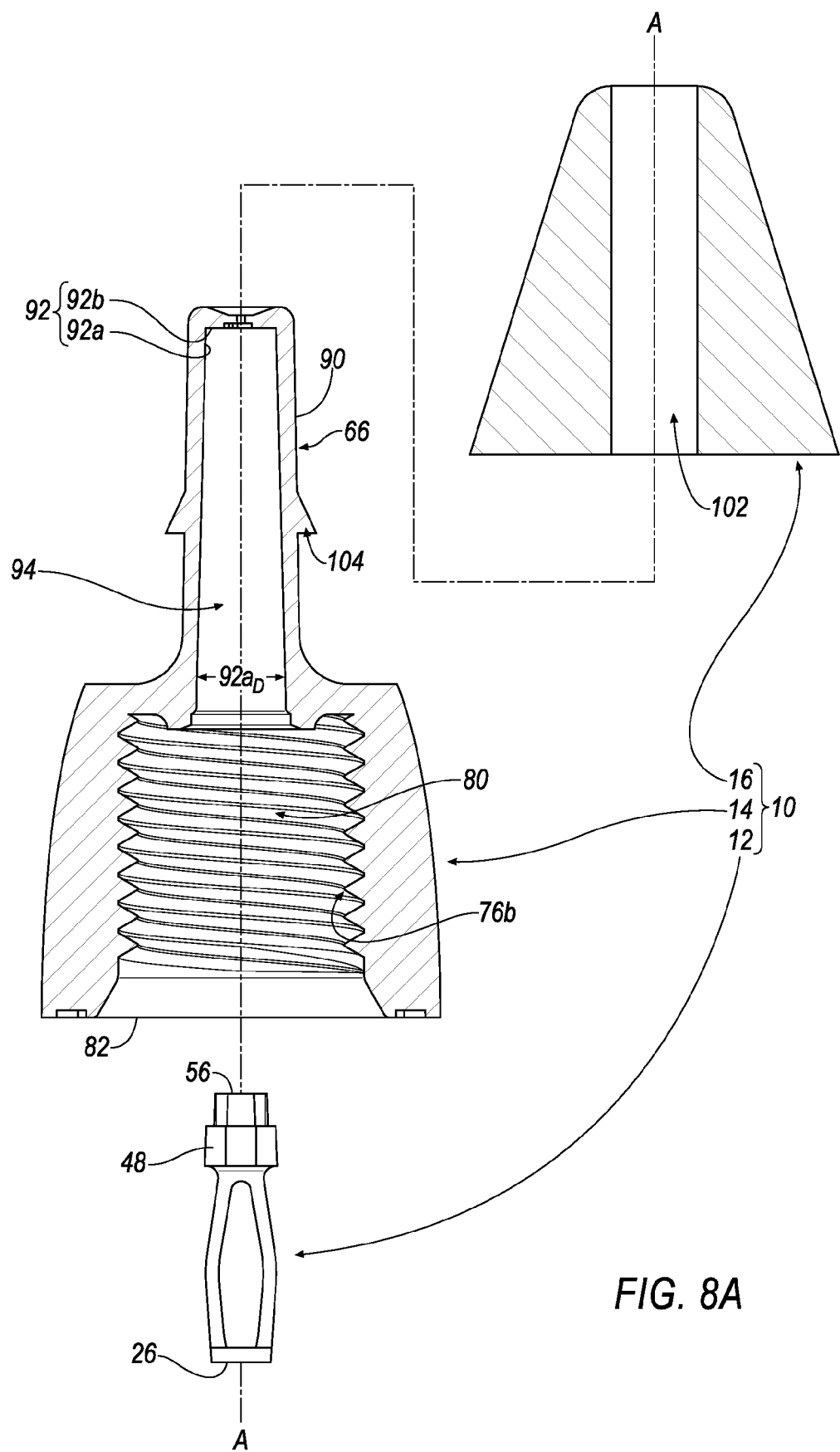
FIG. 8A is an exploded, side, partial cross-sectional view of the nozzle assembly according to line 8A-8A of FIG. 1A.
Figure 8B:
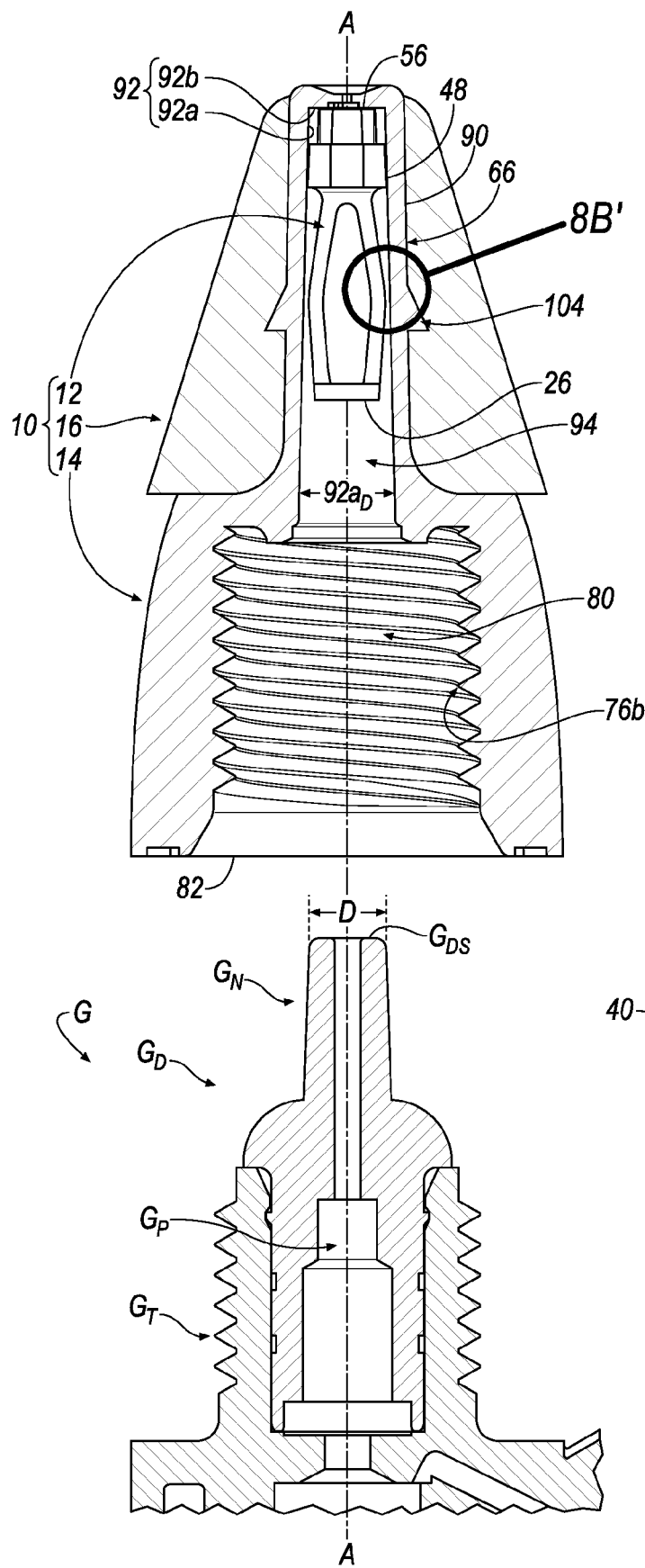
FIG. 8B is a first assembled, side, partial cross-sectional view of the nozzle assembly according to FIG. 8A.
Figure 8B:
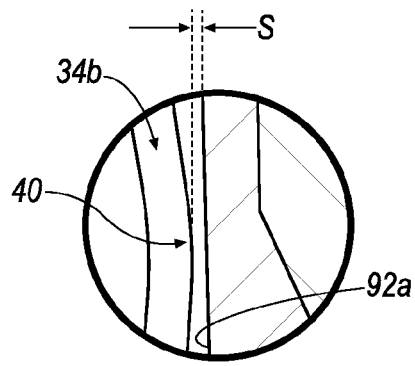

Referring to FIGS. 1A-1B and 8A-8D, an exemplary method for assembling the nozzle assembly 10 is described. As seen in FIG. 8A, a first step for assembling the nozzle assembly 10 may include arranging the distal surface 56 of the head portion 54 of the distal portion 22 of the fluid atomizer 12 opposite the proximal passage opening 82 of the nozzle member 14. Then, as seen in FIG. 8B, the fluid atomizer 12 may be firstly axially inserted into the passage 80 formed by the proximal base portion 64 of the nozzle member 14 and then secondly axially inserted into the passage 94 formed by the distal stem portion 66 of the nozzle member 14. In some instances, the diameter $42_D$ (see, e.g., FIGS. 2 and 3A) formed by side surface 48 of the shoulder portion 42 of the fluid atomizer 12 may be approximately equal to but slightly less than the substantially constant diameter $92a_D$ of the passage 94 formed by the distal stem portion 66 of the nozzle member 14; in some examples, upon inserting the fluid atomizer 12 into the passage 94 formed by the distal stem portion 66 of the nozzle member 14, at least one surface portion (e.g., one or more of the side surface 48 of the shoulder portion 42 and the distal surface 56 of the head portion 54) of the fluid atomizer 12 may be disposed adjacent a surface (e.g., the inner side surface 92 of the substantially tube-shaped body 86 of the distal stem portion 66) of the nozzle member 14 for connecting the fluid atomizer 12 to the nozzle member 14 for forming the nozzle assembly 10.

As seen in FIG. 8B, the conical cap member 16 may connected to and disposed about the outer side surface 90 of the substantially tube-shaped body 86 of the distal stem portion 66 of the nozzle member 14. The conical cap member 16 includes an axial passage 102 (see, e.g., FIG. 8A) that permits insertion of the distal stem portion 66 of the nozzle member 14 there-through when connecting the conical cap member 16 to the distal stem portion 66. In some instances, one or more radially outwardly projecting barbs 104 may extend from the outer side surface 90 of the substantially tube-shaped body 86 of the distal stem portion 66 of the nozzle member 14 in order to bite into and radially secure the conical cap member 16 to the nozzle member 14 once the distal stem portion 66 of the nozzle member 14 is arranged within the axial passage 102 of the conical cap member 16. The conical cap member 16 may include a conical shape in order to easily facilitate insertion of the nozzle assembly 10 into an orifice (e.g., a nostril) of an animalia; if the nozzle assembly 10 is to be utilized for the purpose of delivering a nasal drug, a nasal medicine, a nasal vaccination or the like, the conical cap member 16 may be sized for insertion into a nostril of an animalia.

Although the conical cap member 16 is illustrated in a separated orientation with respect to the nozzle member 14 in FIG. 8A, the conical cap member 16 may be connected to and disposed about the outer side surface 90 of the substantially tube-shaped body 86 of the distal stem portion 66 of the nozzle member 14 before insertion of the fluid atomizer 12 within the passage 94 of the nozzle member 14. Further, it should be noted that the conical cap member 16 may be considered an optional component of the nozzle assembly 10, and, accordingly, some implementations of the nozzle assembly 10 may include the fluid atomizer 12 and the nozzle member 14.

Once the nozzle assembly 10 is assembled as described above at FIGS. 8A-8B, the proximal passage opening 82 of the nozzle member 14 is arranged opposite a distal portion $G_D$ (see, e.g., FIG. 8B) of the spray gun, G. In some instances, the distal portion $G_D$ of the spray gun, G, includes an outer threaded surface $G_T$. The outer threaded surface $G_T$ of the distal portion $G_D$ of the spray gun, G, corresponds to the threaded inner side surface 76b of the substantially tube-shaped body 68 of the nozzle member 14 in order to permit the nozzle member 14 (and, thereby, the nozzle assembly 10) to be removably-connected to the spray gun, G.

Figure 8C:
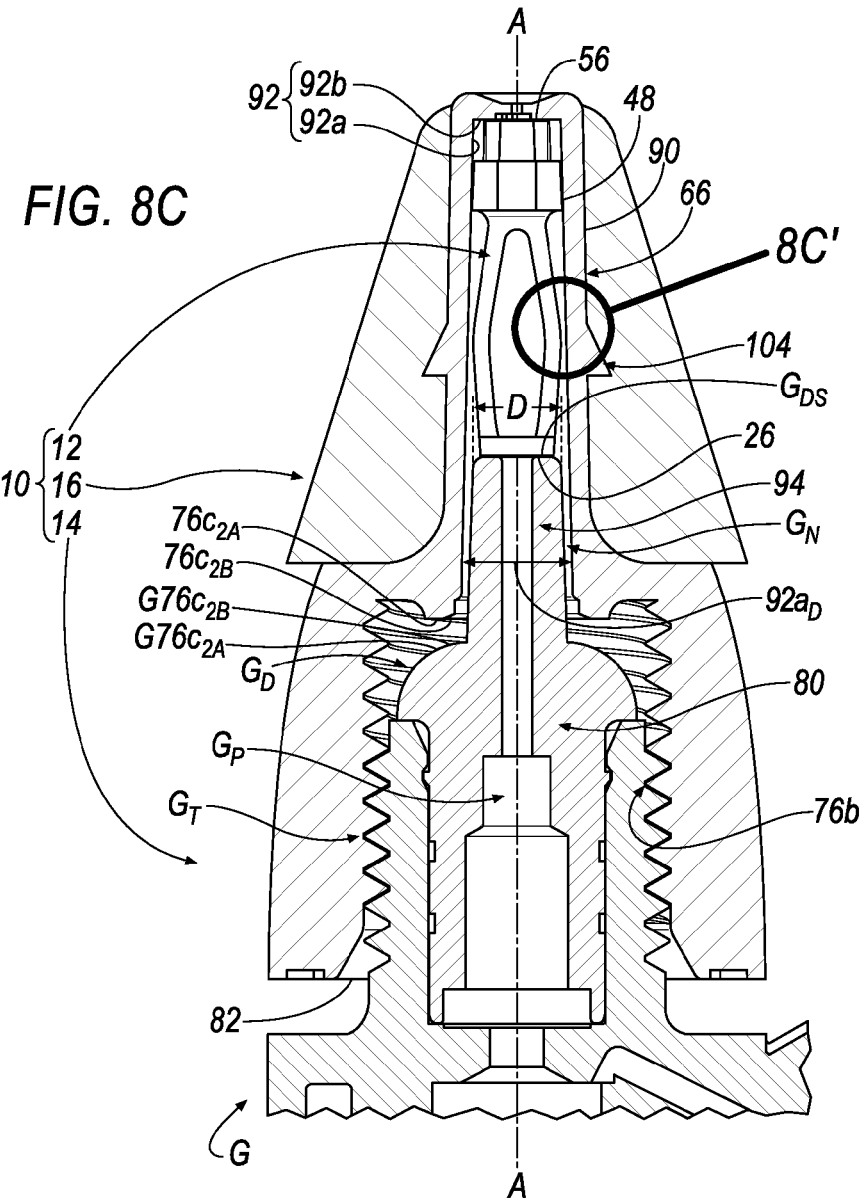
FIG. 8C is a second assembled, side, partial cross-sectional view of the nozzle assembly and spray gun according to line 8C-8C of FIG. 1B.
Figure 8C:
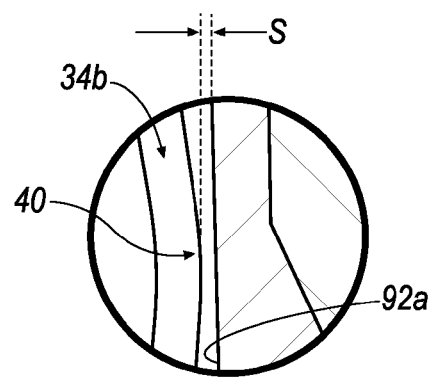

As seen in FIG. 8B, a non-threaded surface portion $G_N$ of the distal portion $G_D$ of the spray gun, G, includes a diameter, D, that is slightly less than that of the substantially constant diameter $92a_D$ of the passage 94 of the nozzle member 14. Accordingly, as seen in FIG. 8C, as the threaded inner side surface 76b of the nozzle member 14 is threadingly-connected to the outer threaded surface $G_T$ of the distal portion $G_D$ of the spray gun, G, a distal surface $G_{DS}$ of the non-threaded surface portion $G_N$ of the of the distal portion $G_D$ of the spray gun, G, enters the passage 94 and subsequently engages the proximal surface 26 of the substantially circular body 24 of the proximal portion 18 of the fluid atomizer 12. Engagement of the distal portion $G_D$ of the spray gun, G, with the proximal surface 26 of the substantially circular body 24 of the proximal portion 18 of the fluid atomizer 12 results in the distal portion $G_D$ of the spray gun, G, axially pushing the fluid atomizer 12 through the passage 94 until the distal surface 56 of the head portion 54 of the distal portion 22 of the fluid atomizer 12 engages the inner distal surface 92b of the substantially tube-shaped body 86 of the distal stem portion 66 nozzle member 14. Additionally, as seen in FIGS. 8C-8D, once the nozzle member 14 is fully threadingly-connected to the spray gun, G, the chamfered surface portion $76c_{2B}$ of the substantially circumferential rib portion of the inner surface 76 of the nozzle member 14 axially engages a rounded surface portion of the distal portion $G_D$ of the spray gun, G, thereby sealing the passage 94 that extends through the substantially tube-shaped body 86 of the nozzle member 14 from the passage 80 that extends through the substantially tube-shaped body 68; as a result of the seal described above, residual fluid, F, is not permitted to leak from the passage 94 and into the passage 80 after actuation of the spray gun, G.

As seen in FIG. 8B', prior to the distal surface 56 of the fluid atomizer 12 being axially urged toward the inner distal surface 92b of the nozzle member 14 by the spray gun, G, the intermediate knee portion 40 of each leg member 34a, 34b of the pair of opposing legs 34 does not engage the inner side surface 92a of the substantially tube-shaped body 86 of the distal stem portion 66 of the nozzle member 14 such that a gap or spacing, S, is located between the intermediate knee portion 40 of each leg member 34a, 34b of the pair of opposing legs 34 and the inner side surface 92a of the substantially tube-shaped body 86 of the distal stem portion 66 of the nozzle member 14. As seen in FIG. 8C', upon initial engagement of the distal surface 56 of the fluid atomizer 12 with the inner distal surface 92b of the nozzle member 14 as described above in FIG. 8C, the intermediate knee portion 40 of each leg member 34a, 34b of the pair of opposing legs 34 still does not engage the inner side surface 92a of the substantially tube-shaped body 86 of the distal stem portion 66 of the nozzle member 14 such the gap or spacing, S, still remains between the intermediate knee portion 40 of each leg member 34a, 34b of the pair of opposing legs 34 and the inner side surface 92*a* of the substantially tube-shaped body 86 of the distal stem portion 66 of the nozzle member 14.

Figure 8D:
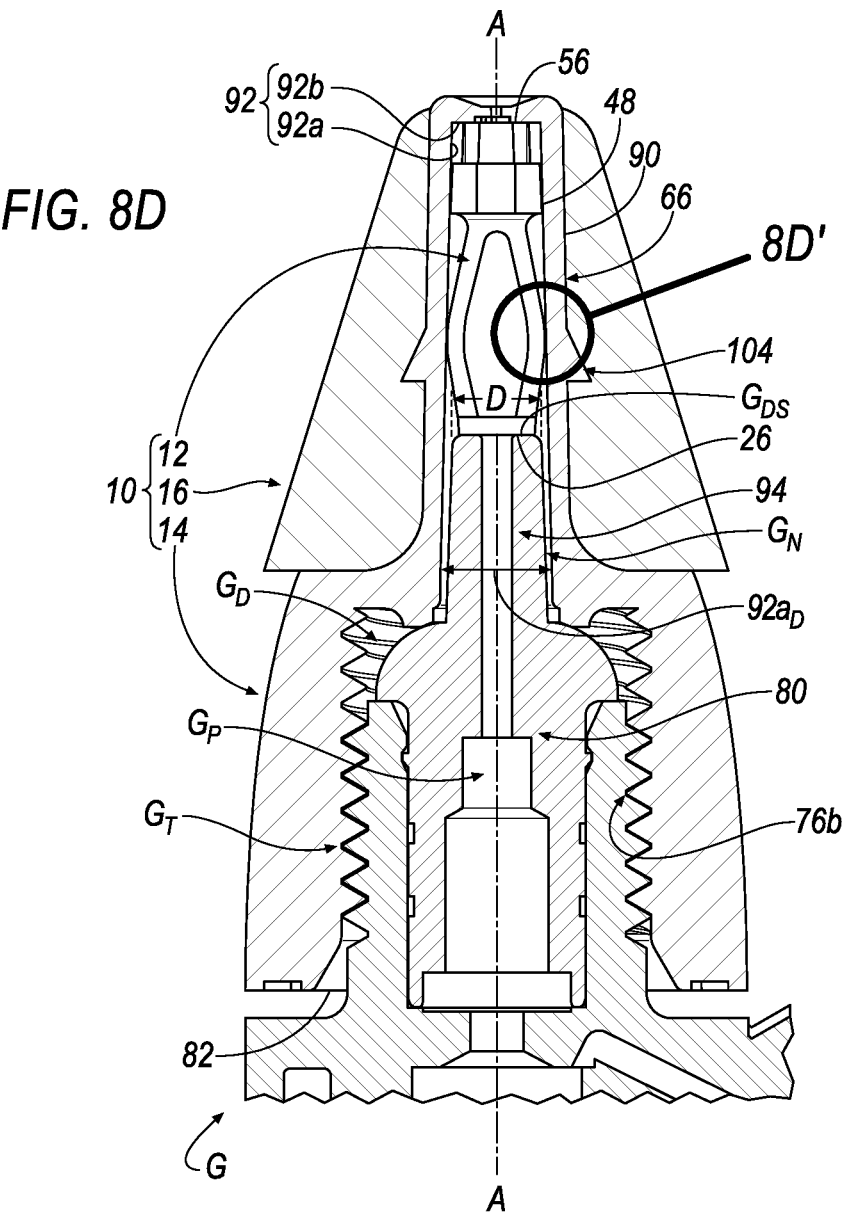
FIG. 8D is a third assembled, side, partial cross-sectional view of the nozzle assembly and spray gun according to line 8D-8D of FIG. 1B.
Figure 8D:
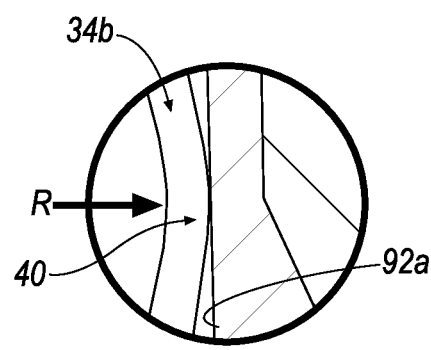

As seen in FIG. 8D', after engagement of the distal surface 56 of the fluid atomizer 12 with the inner distal surface 92*b* of the nozzle member 14, any further axially-directed force imparted to the fluid atomizer 12 by the spray gun, G (caused as a result of further rotation of the nozzle member 14 relative the distal portion $G_D$ of the spray gun, G, by way of the threaded coupling described above), may cause the fluid atomizer 12 to be subtly compressed between the distal surface $G_{DS}$ of the non-threaded surface portion $G_N$ of the of the distal portion $G_D$ of the spray gun, G, and the inner distal surface 92*b* of the nozzle member 14. As a result of the compression of the fluid atomizer 12 as described above, the pair of opposing legs 34 of the fluid atomizer 12 flexes radially outwardly, R (as seen in FIG. 8D' comparatively with respect to FIGS. 8B' and 8C'), such that the intermediate knee portion 40 of each leg member 34*a*, 34*b* of the pair of opposing legs 34 engages the inner side surface 92*a* of the substantially tube-shaped body 86 of the distal stem portion 66 nozzle member 14 that defines the passage 94. As a result of the engagement of the intermediate knee portion 40 of each leg member 34*a*, 34*b* of the pair of opposing legs 34 engaging the inner side surface 92*a* of the substantially tube-shaped body 86 of the distal stem portion 66 nozzle member 14, any spinning movement of the fluid atomizer 12 about the central axis, A-A, relative the nozzle member 14 is prohibited when a fluid is guided from the container, C, through the spray gun, G, and out of the nozzle assembly 10.

Figure 9:
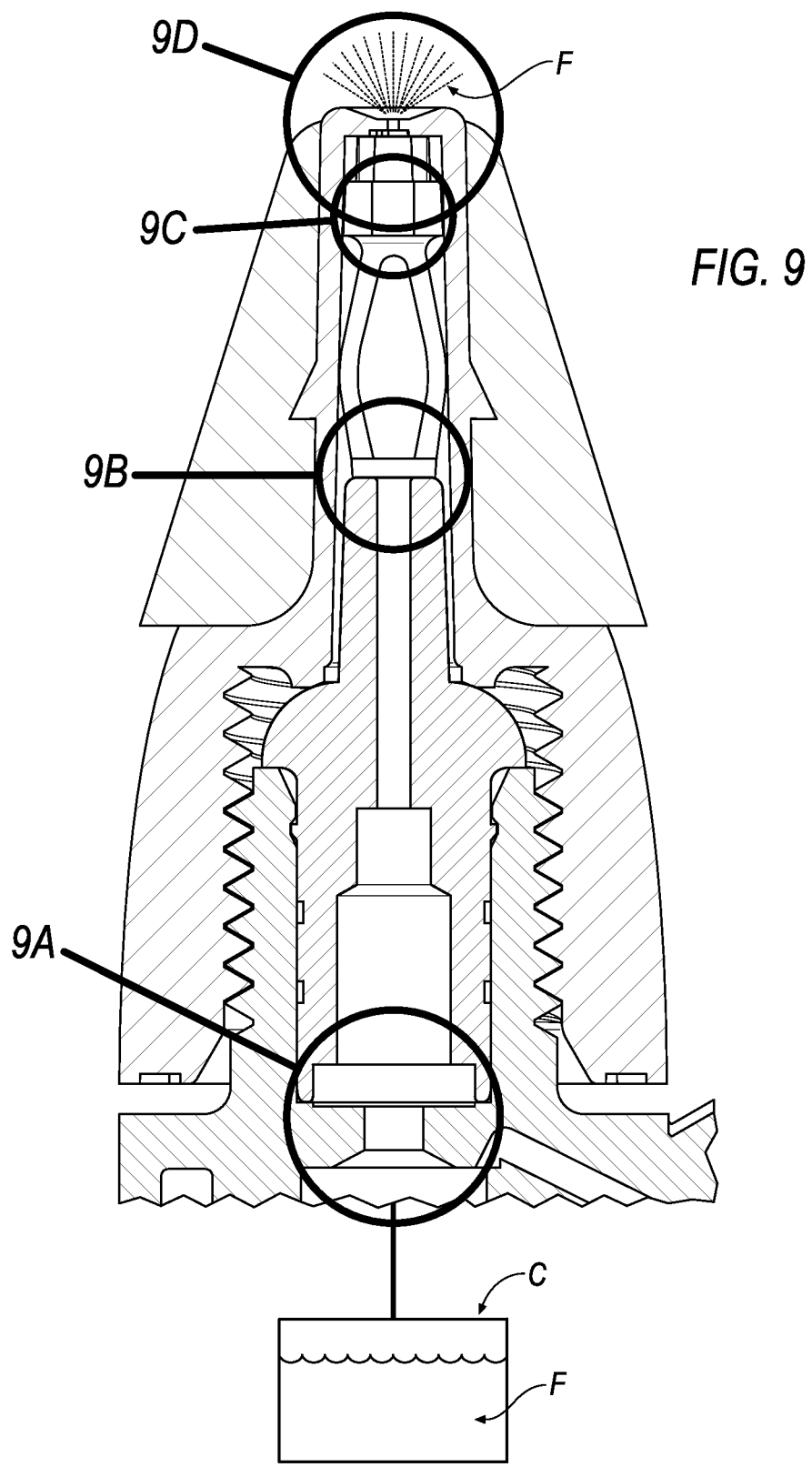
FIG. 9 is an assembled, side, partial cross-sectional view of the nozzle assembly and spray gun according to line 9-9 of FIG. 1B.
Figure 9D:
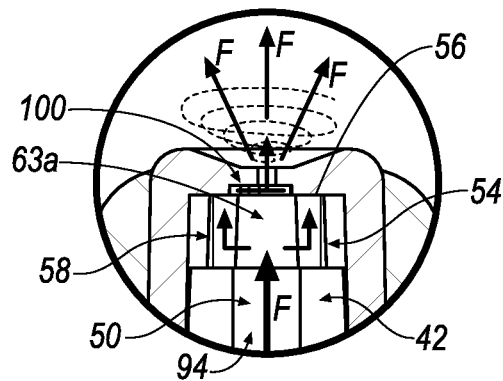
FIG. 9D is an enlarged view of FIG. 9 according to line 9D.
Figure 9C:
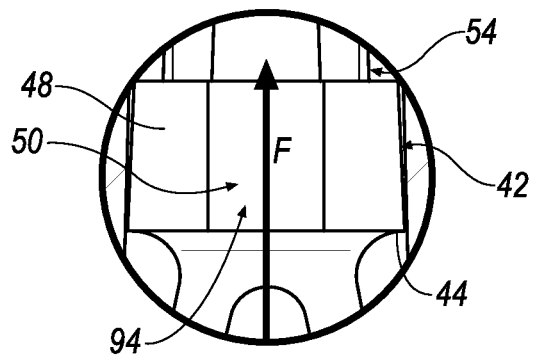
FIG. 9C is an enlarged view of FIG. 9 according to line 9C.
Figure 9B:
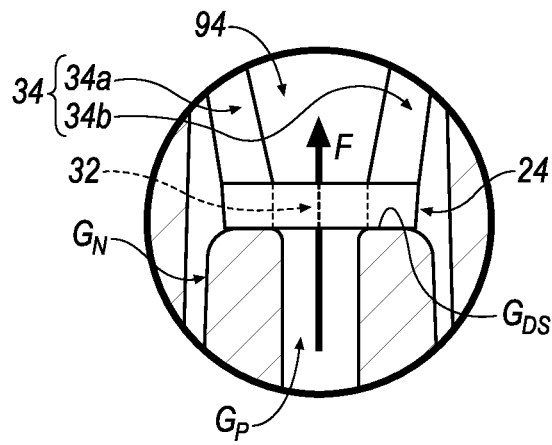
FIG. 9B is an enlarged view of FIG. 9 according to line 9B.
Figure 9A:
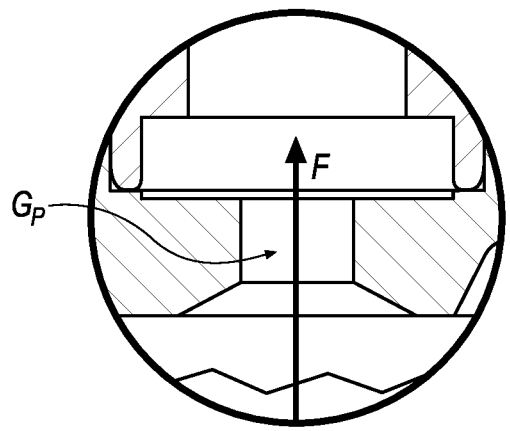
FIG. 9A is an enlarged view of FIG. 9 according to line 9A.

With reference to FIGS. 9 and 9A-9D, once the nozzle assembly 10 is connected to the spray gun, G, as described above, fluid, F, is guided from the container, C, through the spray gun, G, and out of the nozzle assembly 10 according to the following exemplary embodiment. Firstly, as seen in FIG. 9A, after actuating the spray gun, G (e.g., by, for example, pressing a handle member, $G_H$ (see, e.g., FIGS. 1A-1B) of the spray gun, G), fluid, F, may be guided from the container, C, such that the fluid, F, enters a passage $G_P$ formed in the distal portion $G_D$ of the spray gun, G. As described above, the passage $G_P$ formed in the distal portion $G_D$ of the spray gun, G, extends through the passage 80 that extends through the substantially tube-shaped body 68 of the nozzle member 14; therefore, as the fluid, F, travels through the passage $G_P$ formed in the distal portion $G_D$ of the spray gun, G, the fluid, F, is also travelling through the passage 80 that extends through the substantially tube-shaped body 68 of the nozzle member 14.

Then, as seen in FIG. 9B, the fluid, F, may exit the passage $G_P$ at the distal surface $G_{DS}$ of the non-threaded surface portion $G_N$ of the distal portion $G_D$ of the spray gun, G. The passage $G_P$ may terminate at the distal surface $G_{DS}$ of the non-threaded surface portion $G_N$ of the of the distal portion $G_D$ of the spray gun, G, and may be axially aligned with the passage 32 that extends through the substantially circular body 24 of the proximal portion of the fluid atomizer 12 such that the fluid, F, may travel beyond the distal surface $G_{DS}$ of the non-threaded surface portion $G_N$ of the of the distal portion $G_D$ of the spray gun, G, and through the passage 32 that extends through the substantially circular body 24 of the proximal portion of the fluid atomizer 12. After the fluid, F, travels through the passage 32 that extends through the substantially circular body 24 of the proximal portion of the fluid atomizer 12, the fluid, F, may axially flow through the passage 94 that extends through the substantially tube-shaped body 86 of the distal stem portion 66 nozzle member 14 and about the pair of opposing legs 34 of the intermediate portion 20 fluid atomizer 12 and toward the proximal surface 44 of the distal portion 22 of the fluid atomizer 12.

Referring to FIG. 9C, the fluid, F, then axially travels toward the proximal surface 44 of the distal portion 22, the fluid atomizer 12 and is axially channeled toward the radially inwardly projecting recess 50 formed in the side surface 48 of the shoulder portion 42 of the fluid atomizer 12 as a result of the side surface 48 of the shoulder portion 42 of the distal portion 22 of the fluid atomizer 12 being disposed adjacent or close to the inner side surface 92*a* of the substantially tube-shaped body 86 of the of the distal stem portion 66 nozzle member 14. Accordingly, the fluid, F, may be guided axially along the radially inwardly projecting recess 50 formed in the side surface 48 of the shoulder portion 42 toward the head portion 54 of the distal portion 22 of the fluid atomizer 12 such that the fluid, F, is permitted to further axially flow through the passage 94 that extends through the substantially tube-shaped body 86 of the distal stem portion 66 nozzle member 14.

Referring to FIG. 9D, after the fluid, F, travels through the radially inwardly projecting recess 50 formed in the side surface 48 of the shoulder portion 42 of the fluid atomizer 12, the fluid, F, may axially flow through the passage 94 that extends through the substantially tube-shaped body 86 of the distal stem portion 66 nozzle member 14 and about the side surface 58 of the head portion 54 of the distal portion 22 of the fluid atomizer 12 and toward the distal surface 56 of the head portion 54 of the distal portion 22 of the fluid atomizer 12. Because one of the arcuate surfaces 63*a*-63*c* (e.g., the arcuate surface 63*a*) of the plurality of arcuate surfaces 63 of the head portion 54 is aligned with the radially inwardly projecting recess 50 of the shoulder portion 42, the fluid, F, that is axially guided along the arcuate surface 63*a* is radially diverted around the head portion 54 as the fluid further axially flows through the passage 94 that extends through the substantially tube-shaped body 86 of the distal stem portion 66 nozzle member 14.

As the fluid, F, is radially diverted around the head portion 54 as described above, the fluid, F, is axially channeled toward each radially inwardly projecting recess 60*a*, 60*b*, 60*c* of the plurality of radially inwardly projecting recesses 60 of the head portion 54 and toward the distal surface 56 of the head portion 54. Once the fluid, F, flows through the passage 94 that extends through the substantially tube-shaped body 86 of the distal stem portion 66 nozzle member 14 such that the fluid, F, arrives at the distal surface 56 of the head portion 54, the fluid, F, is guided out of the passage 94 upon entering the recess 100 formed in the inner distal surface 92*b* of the inner side surface 92 of the substantially tube-shaped body 86 of the distal stem portion 66.

Once the fluid, F, enters the recess 100 formed in the inner distal surface 92*b* of the inner side surface 92 of the substantially tube-shaped body 86 of the distal stem portion 66, the fluid, F, firstly enters the plurality of radial recess portions 100*a* of the recess 100 such that the fluid, F, is radially guided toward the central axis, A-A. The fluid, F, that is radially guided by the plurality of radial recess portions 100*a* of the recess 100 collides at the central recess portion 100*b* of the recess 100 and then subsequently exits the nozzle member 14 at the axial recess passage portion 100*c*. As a result of the arrangement of the fluid atomizer 12 within the nozzle member 14, and, as a result of the collision of the fluid, F, arising from the arrangement of the plurality of radial recess portions 100*a*, the fluid, F, exits the nozzle member 14 with an atomized, swirling spray pattern.

After one or more uses of the spray gun, G, as described above, one or more of the passages 80, 94 and openings 82, 84, 96, 98 may be clogged (with, e.g., mucus, if, for example, the nozzle assembly 10 is arranged within the nasal passage of animalia). Therefore, a user may disconnect the nozzle assembly 10 from the spray gun, G, by threadingly decoupling the nozzle assembly 10 from the spray gun, G. When the nozzle assembly 10 is decoupled from the spray gun, G, the pair of opposing legs 34 of the fluid atomizer 12 may no longer be flexed in the radially outwardly direction (as seen in FIG. 8D') and return to a relaxed, non-flexed orientation (as seen in FIGS. 8B' and 8C'); as a result, the fluid atomizer 12 may slide out of the passages 80, 94 of the nozzle member 14.

Once the fluid atomizer 12 has been disconnected from the nozzle member 14, the fluid atomizer 12 may be cleaned. Further, once the fluid atomizer 12 has been disconnected from the nozzle member 14, unobstructed access to one or more the passages 80, 94 and openings 82, 84, 96, 98 may be provided in order to facilitate cleaning of the nozzle member 14.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A fluid atomizer, comprising:
a proximal portion including
a body;
an intermediate portion including
legs connected to the body of the proximal portion; and
a distal portion including
a shoulder portion connected to the legs of the intermediate portion, wherein the shoulder portion includes a distal surface,
wherein the intermediate portion is between the proximal portion and the distal portion, and wherein the distal portion further includes
a head portion adjacent to the shoulder portion, wherein the head portion includes, a distal surface and a side surface between the distal surface of the shoulder portion and the distal surface of the head portion, and wherein the side surface of the head portion includes a plurality of radially inwardly projecting recesses, each of the recesses extending along an entire height of the head portion from the distal surface of the shoulder portion to the distal surface of the head portion.

2. The fluid atomizer according to claim 1, wherein the proximal portion is integrally-formed with the intermediate portion, wherein the intermediate portion is integrally-formed with the distal portion.

3. The fluid atomizer according to claim 1, wherein the body includes: a proximal surface, a distal surface, an outer side surface and an inner side surface, wherein the inner side surface defines a passage that extends through the body from the proximal surface to the distal surface.

4. The fluid atomizer according to claim 3, wherein each leg of the legs include: a proximal portion, a distal portion and an intermediate knee portion between the proximal portion and the distal portion, wherein the proximal portion of each leg of the legs is integral with and extends away from the distal surface of the body.

5. The fluid atomizer according to claim 4, wherein as each of the proximal portion and the distal portion of each leg of the legs extend axially away from the proximal portion and the distal portion, each of the proximal portion and the distal portion of each leg of the legs extend with a radially outward component such that the intermediate knee portion of each leg defines a peak of each leg that is arranged at a position that is radially beyond a width defined by the outer side surface of the body.

6. The fluid atomizer according to claim 4, wherein the distal portion of each leg of the legs are integral with and extend away from a proximal surface of the shoulder portion.

7. The fluid atomizer according to claim 6, wherein the shoulder portion further includes a side surface between the proximal surface of the shoulder portion and the distal surface of the shoulder portion.

8. The fluid atomizer according to claim 7, wherein the side surface of the shoulder portion forms a radially inwardly projecting recess that extends along an entire height of the shoulder portion.

9. The fluid atomizer according to claim 8, wherein the head portion axially extends from and is integral with the distal surface of the shoulder portion.

10. The fluid atomizer according to claim 9, wherein the side surface of the head portion is interrupted by a plurality of arcuate surfaces, wherein each arcuate surface of the plurality of arcuate surfaces is arranged between each radially inwardly projecting recess of the plurality of radially inwardly projecting recesses.

11. The fluid atomizer according to claim 10, wherein one of the arcuate surfaces of the plurality of arcuate surfaces of the head portion is aligned with the radially inwardly projecting recess of the shoulder portion.

12. The fluid atomizer according to claim 1, wherein the body of the proximal portion is a substantially circular body.

13. The fluid atomizer according to claim 1, wherein the legs of the intermediate portion include a pair of opposing legs.

14. A nozzle assembly, comprising:
a nozzle member including a proximal base portion and a distal stem portion, wherein the proximal base portion includes an inner side surface that defines a passage that extends axially through the proximal base portion, wherein distal stem portion includes an inner surface that defines a passage that extends through the distal stem portion; and
a fluid atomizer including: a proximal portion, an intermediate portion and a distal portion, wherein the proximal portion includes a body, wherein the intermediate portion includes legs connected to the body of the proximal portion, wherein the distal portion includes a shoulder portion connected to the legs of the intermediate portion, wherein the shoulder portion includes a distal surface, wherein the intermediate portion is between the proximal portion and the distal portion, wherein the distal portion further includes a head portion adjacent to the shoulder portion, wherein the head portion includes, a distal surface and a side surface between the distal surface of the shoulder portion and the distal surface of the head portion, wherein the head portion includes a plurality of radially inwardly projecting recesses, each of the recesses extending along an entire height of the head portion from the distal surface of the shoulder portion to the distal surface of the head portion, and wherein the legs of the intermediate portion of the fluid atomizer are configured to connect to the nozzle member when the fluid atomizer is arranged inside of the passage in the distal stem portion of the nozzle member.

15. The nozzle assembly according to claim 14 further comprising:
a conical cap member including an axial passage configured to accept insertion of the distal stem portion of the nozzle member therethrough.

16. The nozzle assembly according to claim 15, wherein the conical cap member is formed from a soft, resilient material.

17. The nozzle assembly according to claim 15, wherein one or more radially outwardly projecting barbs extend from an outer side surface of the distal stem portion of the nozzle member to radially engage the conical cap member to the nozzle member.

18. The nozzle assembly according to claim 14, wherein the body of the proximal portion includes a substantially circular body.

19. The nozzle assembly according to claim 14, wherein the legs of the intermediate portion include a pair of opposing legs.

20. The nozzle assembly according to claim 14, wherein the inner surface of the passage extending through the distal stem portion of the nozzle member is defined by a side surface portion and a distal surface portion, and wherein the distal surface portion has a recess.

21. The nozzle assembly according to claim 20, wherein the recess has:
a central recess portion and
a plurality of radial recess portions.

22. The nozzle assembly according to claim 21, wherein the plurality of radial recess portions radially converge upon and are fluidly connected to the central recess portion.

23. A method of using the nozzle assembly of claim 14, comprising the steps of:
inserting the fluid atomizer into the passage in the distal stem portion of the nozzle member; and
flexing the legs of the intermediate portion of the fluid atomizer in a radially-outward direction for
engaging each leg of the legs with the inner surface of the distal stem portion of the nozzle member.

24. The method according to claim 23, wherein the flexing step is conducted in response to applying an axial force to the proximal portion of the fluid atomizer.

25. The method according to claim 24, wherein the applying step is conducted in response to inserting a distal portion of a spray gun into the passage in the distal stem portion of the nozzle member.

26. The method according to claim 23, wherein the legs of the intermediate portion of the fluid atomizer include a pair of opposing legs.

27. The method according to claim 23, wherein engaging each leg of the legs with the inner surface of the distal stem portion of the nozzle member results in spatially-fixing the fluid atomizer within the passage in the distal stem portion of the nozzle member.

28. A method of using the nozzle assembly of claim 15, comprising the steps of
inserting the distal stem portion of the nozzle member through the axial passage of the conical cap member for connecting the conical cap member to the distal stem portion of the nozzle member.

29. The method according to claim 28, wherein the inserting step results in radially engaging and securing the conical cap member to the nozzle member.

* * * * *